(12) United States Patent
Eckhouse et al.

(10) Patent No.: US 9,326,910 B2
(45) Date of Patent: May 3, 2016

(54) LARGE AREA BODY SHAPING APPLICATOR

(75) Inventors: Shimon Eckhouse, Haifa (IL); Avner Rosenberg, Bet Shearim (IL)

(73) Assignee: SYNERON MEDICAL LTD, Yoqneam Illit (IL)

( * ) Notice: Subject to any disclaimer, the term of this patent is extended or adjusted under 35 U.S.C. 154(b) by 43 days.

(21) Appl. No.: 13/456,158

(22) Filed: Apr. 25, 2012

(65) Prior Publication Data

US 2013/0178764 A1    Jul. 11, 2013

Related U.S. Application Data

(60) Provisional application No. 61/585,340, filed on Jan. 11, 2012.

(51) Int. Cl.
*A61H 7/00*    (2006.01)
*A61N 7/02*    (2006.01)
(Continued)

(52) U.S. Cl.
CPC .................. *A61H 7/008* (2013.01); *A61H 7/00* (2013.01); *A61H 11/00* (2013.01); *A61N 5/025* (2013.01); *A61N 5/0616* (2013.01); *A61N 7/00* (2013.01); *A61B 2018/0016* (2013.01); *A61B 2018/0047* (2013.01); *A61B 2018/00654* (2013.01); *A61B 2018/00714* (2013.01); *A61F 7/00* (2013.01); *A61H 23/0245* (2013.01); *A61H 2201/0176* (2013.01); *A61H 2201/0207* (2013.01); *A61H 2201/0221* (2013.01); *A61H 2201/10* (2013.01); *A61H 2201/165* (2013.01); *A61H 2201/168* (2013.01); *A61H 2201/5002* (2013.01); *A61H 2201/5005* (2013.01); *A61H 2201/5082* (2013.01); *A61H 2205/083* (2013.01);

(Continued)

(58) Field of Classification Search
CPC .......... A61B 2018/00654; A61B 2018/00714; A61B 2018/0047; A61B 2018/0016; A61H 7/008; A61H 7/00; A61H 11/00; A61H 23/0245; A61H 2205/083; A61H 2201/0176; A61H 2201/0207; A61H 2201/0221; A61H 2201/165; A61H 2201/10; A61H 2201/168; A61H 2201/5002; A61H 2201/5082; A61H 2201/5005; A61F 7/00; A61N 5/025; A61N 5/0616; A61N 5/0625; A61N 2005/0645; A61N 2005/0649; A61N 7/00; A61N 2007/0078; A61N 2007/0034
See application file for complete search history.

(56) References Cited

U.S. PATENT DOCUMENTS 2,088,780 A    8/1937 Follese
5,601,526 A    2/1997 Chapelon et al.
(Continued)

OTHER PUBLICATIONS

"TRIOiShape Body Sculpting System". Sybaritic Inc. 2011. 14 pages.*

*Primary Examiner* — Long V Le
*Assistant Examiner* — Angela M Hoffa
(74) *Attorney, Agent, or Firm* — Smith Tempel; Gregory Scott Smith

(57) ABSTRACT

A method and apparatus that affect vacuum to massage a volume of the skin and one or more types of skin treatment energies coupled to the massaged volume to treat the skin and subcutaneous adipose tissue and produce a desired treatment effect. The method and apparatus are based on coupling an array or a number of arrays being an assembly of skin treatment units with each skin treatment unit including a hollow cavity and a number of different energy to skin applying elements operative to receive skin treatment energy from a source of such energy and couple or apply the received energy to a treated segment of skin.

22 Claims, 12 Drawing Sheets

(51) Int. Cl.
  *A61N 5/02* (2006.01)
  *A61N 5/06* (2006.01)
  *A61B 18/00* (2006.01)
  *A61H 11/00* (2006.01)
  *A61N 7/00* (2006.01)
  *A61H 23/02* (2006.01)
  *A61F 7/00* (2006.01)

(52) U.S. Cl.
  CPC ....... *A61N5/0625* (2013.01); *A61N 2005/0645* (2013.01); *A61N 2005/0649* (2013.01); *A61N 2007/0034* (2013.01); *A61N 2007/0078* (2013.01)

(56) References Cited

U.S. PATENT DOCUMENTS

| | | | |
|---|---|---|---|
| 6,443,915 B1 | 9/2002 | Hwang | |
| 7,771,374 B2* | 8/2010 | Slatkine | 601/6 |
| 8,133,191 B2* | 3/2012 | Rosenberg et al. | 601/2 |
| 8,273,037 B2 | 9/2012 | Kreindel et al. | |
| 8,275,442 B2* | 9/2012 | Allison | 600/407 |
| 8,323,273 B2* | 12/2012 | Rylander et al. | 606/9 |
| 8,960,622 B2* | 2/2015 | von Pechmann et al. | 248/288.31 |
| 2003/0032900 A1 | 2/2003 | Ella | |
| 2004/0082940 A1* | 4/2004 | Black et al. | 606/9 |
| 2004/0260210 A1 | 12/2004 | Ella et al. | |
| 2006/0058712 A1 | 3/2006 | Altshuler et al. | |
| 2006/0264926 A1* | 11/2006 | Kochamba | 606/41 |
| 2007/0010810 A1* | 1/2007 | Kochamba | 606/41 |
| 2007/0088348 A1* | 4/2007 | Kochamba | 606/41 |
| 2007/0239077 A1 | 10/2007 | Azhari et al. | |
| 2007/0255355 A1* | 11/2007 | Altshuler et al. | 607/86 |
| 2008/0051680 A1 | 2/2008 | Luebcke | |
| 2008/0139974 A1 | 6/2008 | Da Silva | |
| 2008/0146970 A1 | 6/2008 | Litman et al. | |
| 2008/0215039 A1* | 9/2008 | Slatkine et al. | 606/9 |
| 2008/0312648 A1* | 12/2008 | Peterson | 606/41 |
| 2009/0221938 A1* | 9/2009 | Rosenberg et al. | 601/2 |
| 2009/0275865 A1 | 11/2009 | Zhao et al. | |
| 2010/0016761 A1* | 1/2010 | Rosenberg | 601/2 |
| 2010/0204619 A1* | 8/2010 | Rosenberg | 601/3 |
| 2011/0015549 A1 | 1/2011 | Eckhouse et al. | |
| 2011/0046523 A1* | 2/2011 | Altshuler et al. | 601/3 |
| 2011/0166559 A1* | 7/2011 | Eckhouse et al. | 606/9 |
| 2012/0010603 A1* | 1/2012 | Milner et al. | 606/13 |
| 2012/0116271 A1 | 5/2012 | Caruso et al. | |
| 2012/0123304 A1* | 5/2012 | Rybyanets | 601/2 |
| 2012/0136280 A1* | 5/2012 | Rosenberg et al. | 601/2 |
| 2012/0136282 A1* | 5/2012 | Rosenberg et al. | 601/3 |
| 2012/0150079 A1* | 6/2012 | Rosenberg | 601/6 |
| 2012/0197242 A1* | 8/2012 | Rosenberg | 606/2 |
| 2012/0253416 A1* | 10/2012 | Erez et al. | 607/3 |
| 2012/0277587 A1* | 11/2012 | Adanny et al. | 600/439 |
| 2013/0158440 A1* | 6/2013 | Allison | 601/2 |
| 2013/0178916 A1* | 7/2013 | Rylander et al. | 607/88 |
| 2014/0081250 A1* | 3/2014 | Eckhouse et al. | 606/9 |

* cited by examiner

LARGE AREA BODY SHAPING APPLICATOR

CROSS-REFERENCE TO RELATED APPLICATIONS

This is a non-provisional utility patent filed with the United States Patent Office under 35 USC §111(a) and 37 CFR 1.53(b) and claiming the priority under 35 USC 119(e) of the provisional application that was filed with the United States Patent Office under 35 USC §111(b) on Jan. 11, 2012 by the same inventors and assigned Ser. No. 61/585,340. Patent Cooperation PCT/IL2009/000693 filed on Dec. 7, 2009 and bearing the title APPLICATOR FOR SKIN TREATMENT WITH AUTOMATIC REGULATION OF SKIN PROTRUSION MAGNITUDE is incorporated herein by reference.

TECHNOLOGY FIELD

The large area body shaping applicator relates to the field of equipment for non-invasive aesthetic treatments.

BACKGROUND

Skin massage is a type of manipulation of superficial and deeper layers of skin and subcutaneous tissue layers. Massage involves acting on and manipulating the skin with pressure. The skin may be manipulated, typically kneaded, manually or with mechanical aids. Whether the massage is done manually or with mechanical aids it is applied to a segment of skin or tissue defined by the hands of the caregiver or the size of the mechanical aids. The remaining segments of the skin are treated by moving the hands or repositioning the mechanical aid across a larger skin segment. Target tissues may include muscles, tendons, adipose tissue and other segments of the skin and body. Because of the need to apply pressure to the skin and then repositioning the source of pressure during the treatment (i.e., moving the therapist hands or mechanical aid to a different area of the body), massage is associated with a significant amount of effort and attention that the caregiver has to apply.

Adipose tissue is frequently treated non-invasively by different energies coupled to the skin. Typical types of energies that may be found in use for skin treatment include ultra sound (US) energy, Radio Frequency (RF) energy, or radiation energy emitted by a source of light or heat. The skin treatment energy is coupled to the skin by an applicator. The size of the applicator defines to some extent the segment of skin or tissue to which the skin treatment energy is transferred. In order to treat other skin segments, the applicator is repositioned across a large segment of the skin and activated to couple treatment energy to this segment of skin.

Different types of energy are frequently used for circumference reduction, adipose tissue removal, and other cosmetic procedures where application of skin treatment energy could bring a desired beneficial treatment effect.

BRIEF SUMMARY

The present disclosure describes a method and apparatus, as well as variant features and aspects thereof, to effectively utilize a vacuum pressure to massage a volume of the skin and one or more types of skin treatment energies coupled to the massaged volume to treat the skin and subcutaneous adipose tissue and produce a desired treatment effect. One embodiment of the method and apparatus are based on coupling an array, or a number of arrays, as an assembly of skin treatment units with each skin treatment unit including a hollow cavity and a number of different energy to skin applying elements that are configured to receive skin treatment energy from a source of such energy and couple or apply the received energy to a treated segment of skin.

Vacuum pressure is applied in a desired sequence to the cavities of the skin treatment units. Suction produced by the vacuum pressure draws volumes of skin into the cavities and, subsequently venting the cavity with atmosphere or air releases the volumes of skin from the cavities. A valve capable of switching between vacuum and atmosphere or a source of air pressure facilitates evacuating air from the cavity to draw the volume of skin therein and drawing air into the cavity so that the volume of skin is released. The volumes of skin drawn and released are smaller than the treated skin segment to which the array is applied. The sequence of applying vacuum pressure and then releasing or reducing of the vacuum pressure generates a back and forth massaging movement of the skin segment tissue against the flared rims of the skin treatment units. The operational sequence of applying the vacuum pressure and the releasing or reducing of the vacuum pressure in the cavities along with the application of skin treatment energy to the volumes of skin can advantageously produce various patterns of skin treatments and subcutaneous movements.

Various embodiments of the disclosed method and apparatus couple skin treatment energy to the application/release of vacuum pressure during a massage treatment. Thus, embodiments of the method and apparatus operate to provide an automated massaging of a segment of skin either alone, or in conjunction with the application of skin treatment energy. Such skin treatment energy could be selected from a group of energy types including, but not necessarily limited to light, RF, ultrasound, electrolipophoresis, iontophoresis and microwaves. Each of these energy type, combinations thereof and in some embodiments, maybe even additional and/or alternative energy types can be delivered to the skin by energy to skin applying elements. The energy to skin applying elements could be located in one or more locations including inside the cavities, the flared rims of the cavities, separate units used in conjunction with the vacuum pressure apparatus or any combination thereof.

The topography of a treated skin segment usually is not flat and thus, to conform the array to the topography of the treated skin segment each of the skin treatment units of the array could have at least two degrees of rotational movement with respect to an adjacent unit. Additionally, each of the skin treatment units of the array could have at least two degrees of translational movement with respect to an adjacent unit and skin treatment units connecting joints could allow stretching and tensioning of the array. For instance, the joints may allow movement of the element that connects two skin treatment units to each other and/or, the connecting element may be constructed of a material that can be stretched, such as a material with some level of flexibility or that has elastic like characteristics. The array itself could have either a fixed or variable length. The array could include a mount that has a variable length, the mount sized and shaped to couple and fix the array to a treated skin segment. In other embodiments, the skin treatment units can have any of the following, or combinations thereof, movement capabilities: two directional rotation, three directional rotation, full 360 degree rotational, vertical movement (up and down as in telescoping motion), etc. In addition, in some embodiments, the skin treatment units may be mounted on a flexible substrate thereby allowing the flared rims to settle on the non-uniform surface of the skin treatment area.

According to an example the skin treatment units are made of thermally conductive material and are operative together with the massaging action to reduce or eliminate hot spots and homogenize skin treatment energy across the large treated skin segment distribution. A control unit controls delivery of different types of skin treatment energy that could be delivered in pulse or continuous mode according to a skin treatment protocol. The control unit synchronizes the delivery of energy with the application of vacuum pressure to create a massaging skin movement caused by vacuum. The control unit is operative to control the alternating sequence of vacuum application to the cavities of the skin treatment units as well as the air pressure that according to one example, could be applied to release the skin drawn into the cavity.

GLOSSARY

The term "skin" as used in the present disclosure includes the outer skin layers such as stratum corneum, dermis, epidermis, and the deeper subcutaneous layers such as adipose tissue.

The term "skin treatment energy" as used in the present disclosure means any one of energies facilitating achievement of a desired skin treatment effect. Such energy could be a mechanical energy, a thermal energy, and a mix of them.

The term "energy to skin applying element" as used in the present disclosure means an element operative to receive skin treatment energy from a source of such energy and couple or apply the received energy to a treated segment of skin. An electrode applying RF energy to skin, a ultrasound transducer, a mechanical element, a source of light could be such elements.

BRIEF DESCRIPTION OF THE DRAWINGS

Non-limiting examples of the present disclosure are described in the following description, read with reference to the figures attached hereto and do not limit the scope of the claims. In the figures, identical and similar structures, elements or parts thereof that appear in more than one figure are generally labeled with the same or similar references in the figures in which they appear. Dimensions of components and features illustrated in the figures are chosen primarily for convenience and clarity of presentation and are not necessarily to scale. Referring to the attached figures:

FIG. 3A is a perspective view illustrating the stretching movement of skin treatment units according to an example;

FIGS. 3B and 3C are simplified illustrations of an array of skin treatment units applied to a concave and a convex segment of skin according to an example;

FIGS. 3D and 3E are simplified illustrations of an array of skin treatment units applied to an uneven segment of skin according to an example;

FIGS. 3F and 3G are simplified illustrations of an array of skin treatment units applied to an uneven segment of skin according to an example;

DESCRIPTION

Skin treatment systems could include different units or applicators configured to massage skin including subcutaneous tissue. There could be units or applicators configured to couple to the skin different energies such as ultra sound (US) energy, Radio Frequency (RF) energy, or radiation energy emitted by a source of light or heat. In general, in the operation of the known existing treatment systems and devices, the size of the skin treatment unit or applicator defines the segment of skin or tissue size to which the treatment could be applied. For example, the size of a skin treatment unit could be 20×40 mm or 40×80 mm. In order to treat other or additional skin segments the skin treatment unit is repositioned across a large segment of the skin and activated to couple to this additional segment skin treatment energy.

Repositioning of the skin treatment unit requires a sensible effort on behalf of the caregiver. It complicates his or her work and because the service of providing a massage and/or providing other energy to skin application treatment sessions can take on the order of about 30 to 90 minutes, the time absorbed by repositioning the skin treatment unit results in decreases the treatment quality and efficiency.

The skin treatment across a large skin segment also becomes non-uniform, because it is difficult for the caregiver to keep accurate and consistent skin treatment unit or applicator repositioning movement and treatment timing over a large skin segment.

Repositioning of the skin treatment unit requires certain time and it depends on the skills of the caregiver. Faster applicator repositioning could to some extent improve homogeneity of the skin treatment results and reduce the treatment inefficiency, but the speed with which the caregiver manually repositions the applicator could be insufficient to achieve proper skin treatment homogeneity. In addition to this to this, the efficiency and precision of the caregiver changes during the course of the day or working shift and causes appearance of additional treatment artifacts. As a result, some skin segments are thus treated differently than other skin segments.

The possibility to provide a desired skin treatment protocol to a large segment of skin could facilitate homogenous skin treatment energy distribution across a large skin segment. The energy could be mechanical, such as massage or skin stimulating or heating energy. Different skin massage and skin treatment energy application patterns could facilitate selective treatment of a large segment of skin. They could also release the caregiver from an effort related to displacement of a skin treatment device across the treated skin segment, tracking previous skin treatment device location and determining its next location.

Figure 1:
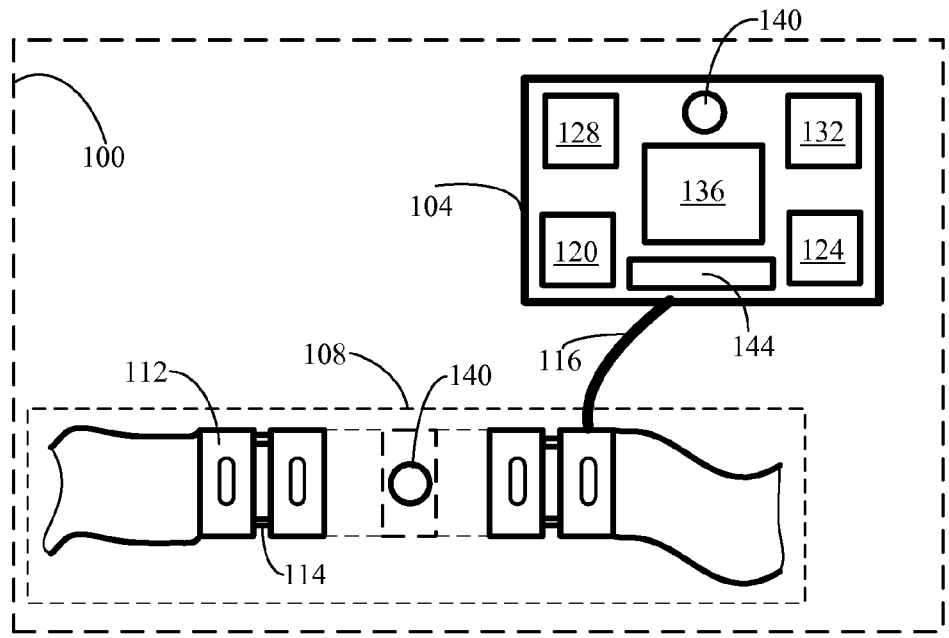
FIG. 1 is a simplified block diagram of an apparatus according to an example.

Referring now to FIG. 1 there is shown a simplified plan view of an apparatus according to an example. Apparatus 100 includes a control unit 104, an array 108 of individually controlled skin treatment units 112 connected between them by a joint 114 facilitating relative displacement and rotation of one skin treatment unit with respect to an adjacent unit, and interconnection umbilical cable 116 connecting between array 108 and control unit 104. It should be appreciated that the control unit 104 can be a processing unit attached as described to the array 108 or can be incorporated into the array 108 itself as a processing unit, hardware device, etc. Control unit 104 could incorporate one or more sources of vacuum, which could be vacuum pumps 120 and one or more air pressure pumps 124, and one or more skin treatment energy sources 128. A processing units PU 132 such as a personal computer or any other device consisting of hardware, firmware or processing capabilities could be operative to govern operation of the sources of vacuum 120, air pressure 124 and skin treatment energy sources 128. PU 132 could accept temperature sensor 524 (FIG. 5) reading signal from each of skin treatment units 112 cavities 408 (FIG. 4 through FIG. 9), and control according to the temperature sensor 524 reading energy sources that supply to each of skin treatment units 108 skin treatment energy. A display 136 could display the treatment process progress and could include a number of soft keys to set the skin treatment protocol. Alternatively a keypad or a keyboard could be used to set the skin treatment protocol. Both control unit 104 and array 108 could include a patient Emergency Button 140, facilitating instant stop of skin treatment procedure/s by the caregiver or by treated subject. In addition, although the control unit 104 is shown as a separate unit connected by means of the umbilical cord 116, it will be appreciated that in some embodiments, the control functions can be on board the array 108 with an interface to a vacuum source and air source or, the entire control unit 104, along with the vacuum source and air source, etc., may be incorporated into the array 108 as well as a combination of any of these configurations as well as other anticipated configurations. In addition, the vacuum source and/or air source may be external and controlled/regulated by a control unit 104 that is mounted on the array and operates to control the amount of pressure applied to the cavities of the skin treatment units.

According to an example, control unit 104 includes a splitter card 144 distributing and controlling activation of vacuum, air pressure, and skin treatment energies to each of the individually controlled skin treatment units 112 of array 108. The splitter card also accepts temperature sensor reading signal from each of the cavities, and controls, according to the temperature sensor reading, energy sources that supply skin treatment energy to each of skin treatment units 112. The distribution and activation of vacuum, air pressure, and skin treatment energies could follow a desired skin treatment protocol and activate, as non-limiting examples, all of the skin treatment units 112, a group of skin treatment units 112, or selected skin treatment units 112. Although shown as a single unit, each of the vacuum, air pressure, and skin treatment energy sources could include a plurality of vacuum, air pressure, and skin treatment energy sources. Emergency button 140 communicates with splitter card 144 or PU 132 and activation of the emergency button 140 instantly discontinues supply of vacuum, air pressure, and skin treatment energies to all of the skin treatment units or applicators 112 of array 108.

Figure 2:
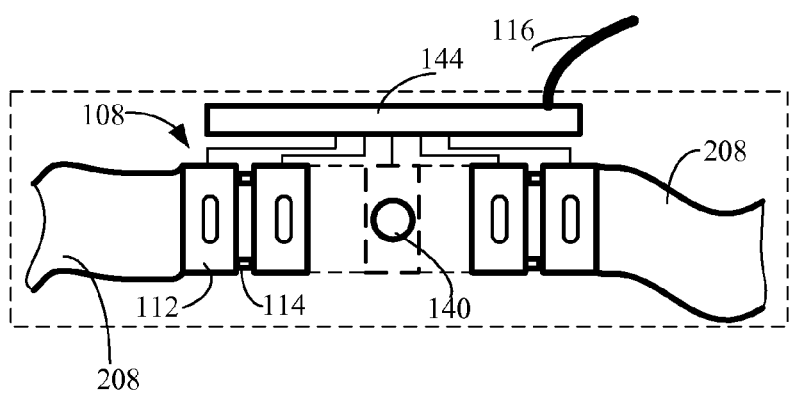
FIG. 2 is a simplified plan view of an array of skin treatment units according to an example.

According to an example, as best illustrated in FIG. 2, splitter card 144 distributing and controlling activation of vacuum, air pressure, and skin treatment energies to each of array 108 of skin treatment units 112 could be associated with the array 108. It could control the vacuum, air pressure, accept a temperature sensor reading signal from each of the cavities, and control according to the temperature sensor reading energy sources that supply to each of skin treatment units 108 skin treatment energy. Associating splitter card 144 with array 108 could simplify the interconnection umbilical cable 116. The distribution and activation of vacuum, air pressure, and skin treatment energies could follow a desired skin treatment protocol and the splitter card could activate all of skin treatment units 112, a group of skin treatment units 112, or selected skin treatment units 112. In addition to this, a simpler controller could be attached to each individual skin treatment unit 112. Emergency button 140 communicates with splitter card 144 and activation of the emergency button 140 can be configured to instantly discontinue supply of vacuum, air pressure, and skin treatment energies to all of the skin treatment units or applicators 112 of array 108.

Splitter card 144 could include and additional PU (not shown), controlling the treatment processes performed by array 108. Such processes could include switching between the application of vacuum pressure or air pressure, switching on and off a particular skin treatment energy supply, selecting between various skin treatment energy supplies, or delivery between the individually controlled skin treatment units, accepting of valve 604 (FIG. 6) signal, accepting temperature sensor reading signals from each of the cavities, detection of the actuation of the emergency button and array release signals, and others.

A mount 208 is sized and shaped to couple and fix the array 108 to a treated skin segment. Mount 208 could be a belt type mount, such that a treated subject could wear array 108 when it is attached and fixed to a segment of skin. Although shown as a belt type, mount 208 could be in form of braces. In one example both belt type mount and braces could be implemented. In yet another embodiment, the array 108 can be incorporated into a massage table or chair and allow a subject to recline on the table. In such an embodiment, the array 108 would conform to the shape of the subject's body in response to the gravitational force of the body against the array 108. In yet another embodiment, the array 108 can simply be laid across the subject and be weighted such that sufficient pressure is applied to the array 108 to force it to conform to the subject's body. In yet another embodiment, the array 108 can be incorporated into a wearable device, such as a jacket type device, a sleeve for sliding over a limb, etc. Other embodiments and variations will be apparent to the reader and these described embodiments are provided as non-limiting examples only.

Figure 3A:
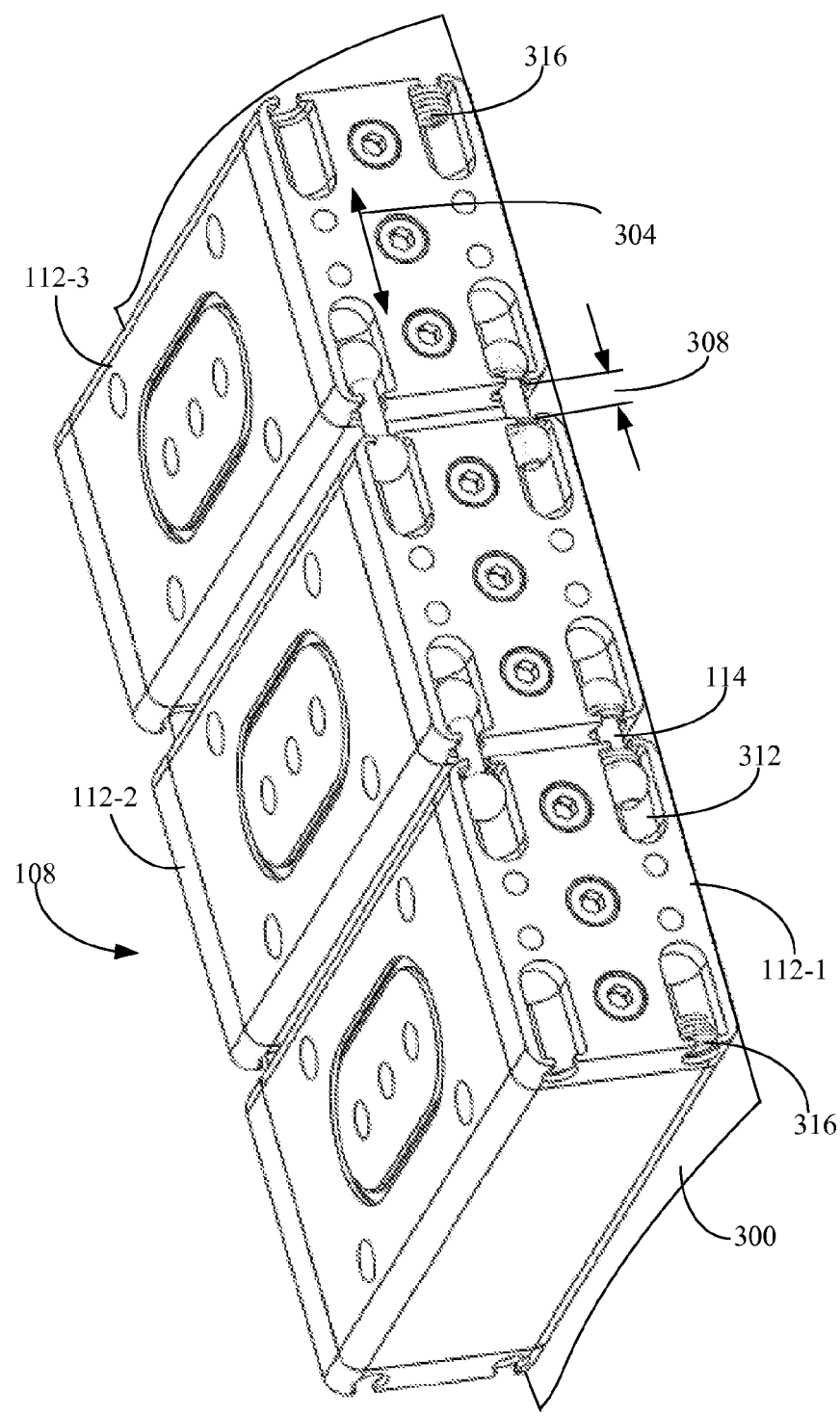
FIGS. 3A-3G, collectively referred to as FIG. 3, illustrate an non-limiting example of the adaptability of an array of skin treatment devices to the contour of target skin being treated.

FIG. 3A is a perspective view illustrating the stretching movement of skin treatment units according to an example. The figure shows an array 108 of skin treatment units 112 or applicators applied to a flat surface 300. The number of skin treatment units 112 has been given for illustration purposes only and it could be a larger or a smaller number then what is illustrated. Skin treatment unit 112-3 has been displaced relative to adjacent unit 112-2 in the directions indicated by arrow 304 (i.e., unit 112-3 would move in the opposite direction from or relative to unit 112-2) opening a gap 308 wider than the gap between units 112-1 and 112-2. The length and flexibility of joint 114 as well as the size of joint nests 312 determine the magnitude of the displacement or stretch. Joint 114 could be a dog-bone type joint that facilitates such movement. Springs 316 could operate to apply in course of treatment certain tension or stretch to array 108 reducing the gap between the skin treatment units 112 and further attaching the skin treatment units 112 to the skin and upon completion of a treatment session to return skin treatment units 112 to their initial position. In one example, joint 114 can be made of a resilient material extending the magnitude of the displacement. In such joint implementation, the joint is subject to a stretch sufficient to support the desired magnitude of the displacement extension and return skin treatment units to an initial position.

Figure 3B:
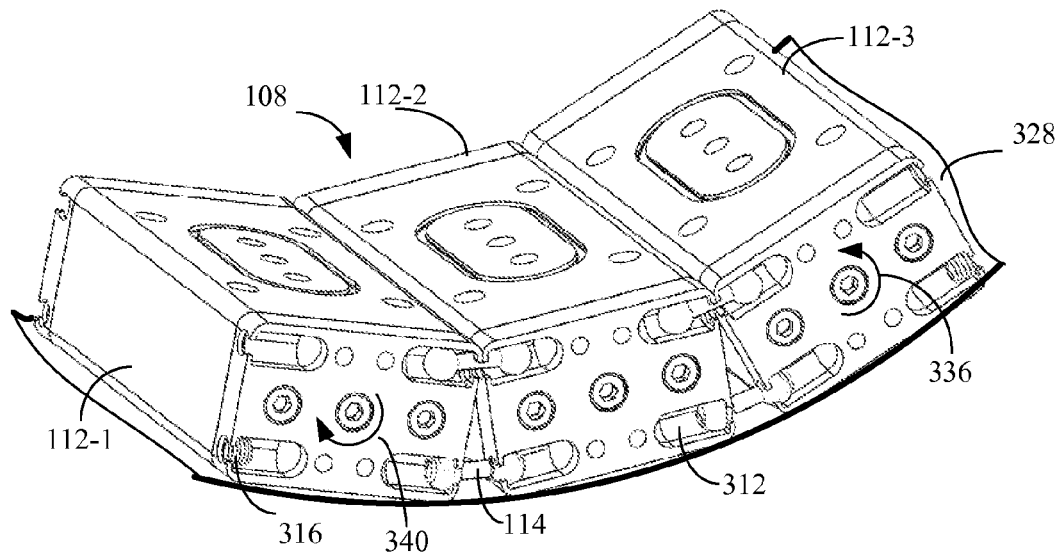
Figure 3C:
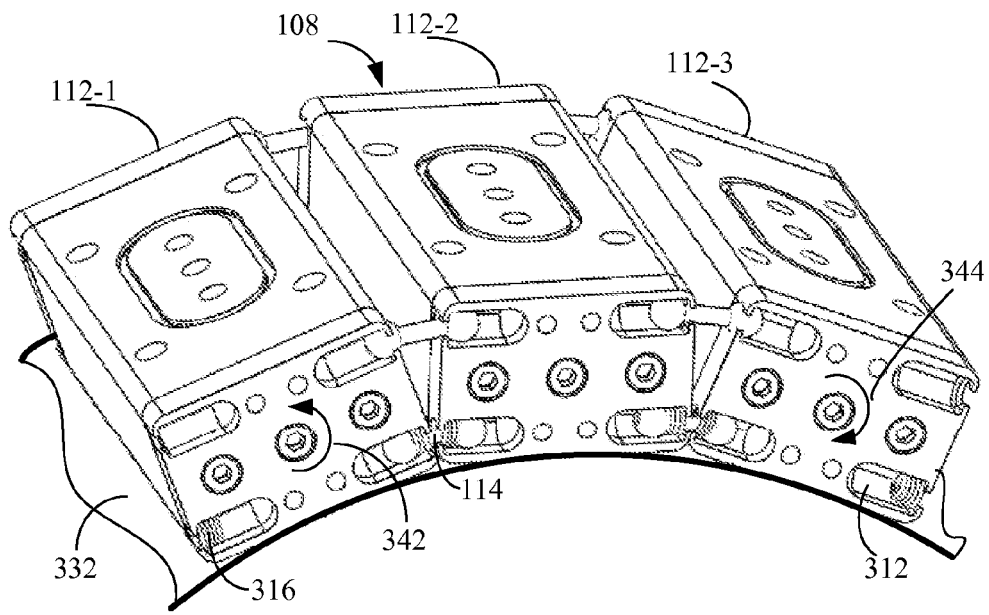

Skin however has a complicated topography and to conform to the topography of the treated skin segment, each of the skin treatment units could have a number of rotational, torsional, and linear movement freedoms. FIGS. 3B and 3C are simplified illustrations of an array of skin treatment units applied to a concave surface 328 and a convex surface 332, such as segments of skin according to an example. Each of the skin treatment units 112-1 through 112-3 of array 108 has a freedom of rotation as shown by arrows 336 and 340 (FIG. 3B) and arrows 342 and 344 (FIG. 3C) with respect to an adjacent unit. These rotational freedoms facilitate array 108 conformance to the topography of the treated skin segment and in particular to a concave skin segment 328 and a convex skin segment 332. Displacement of skin treatment units 112 along joint 114, as explained above could further improve conformance of array 108 to the topography of the treated skin segment.

Figure 3D:
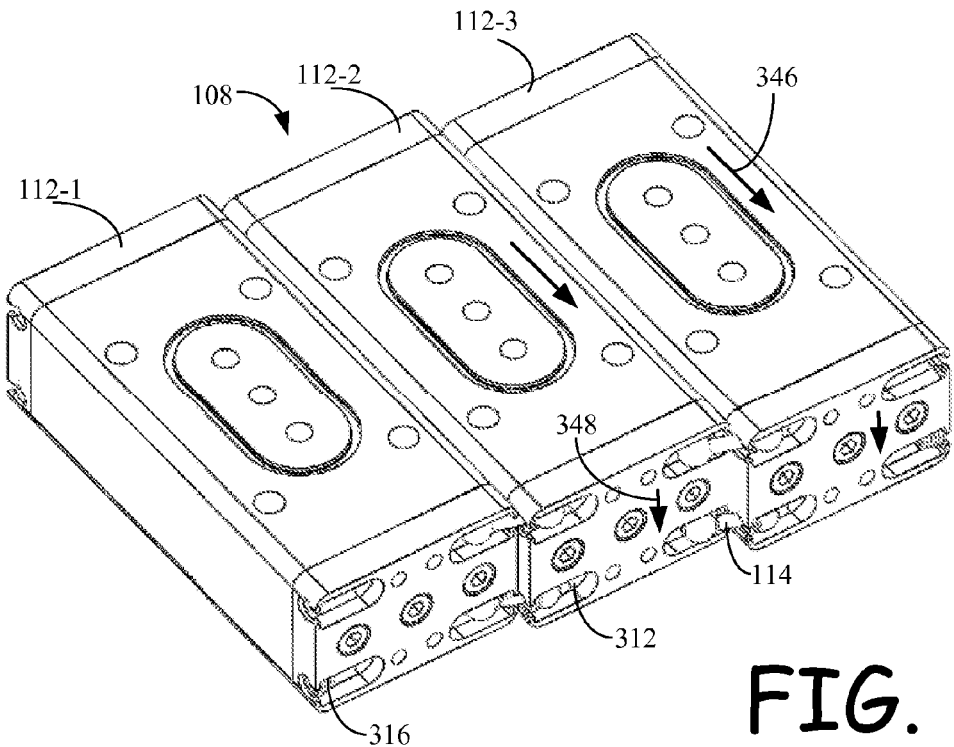
Figure 3E:
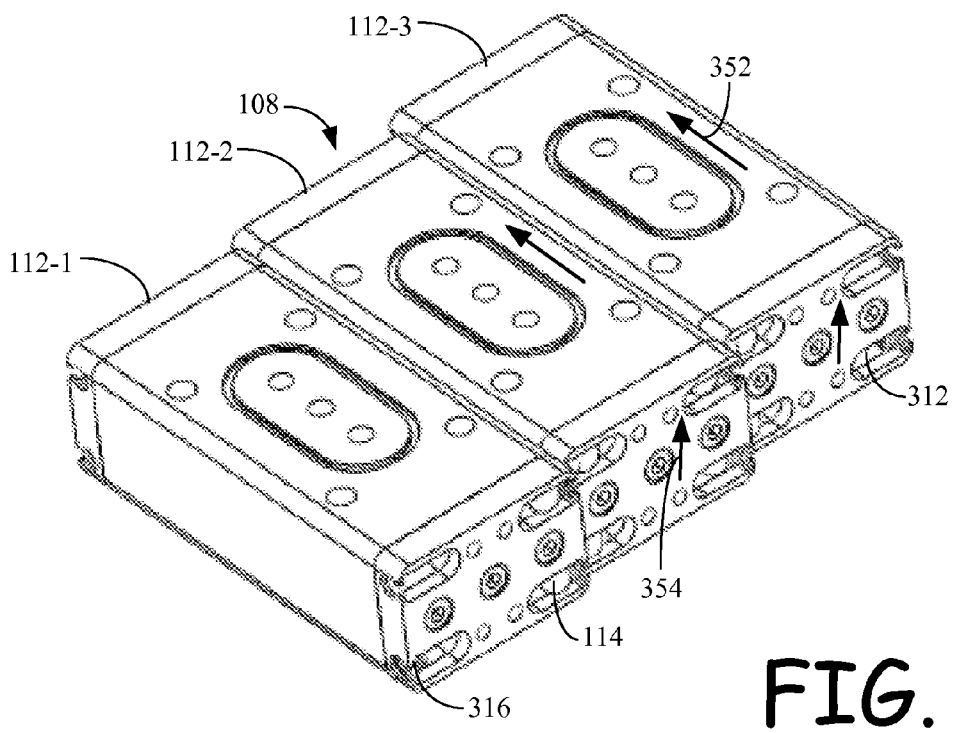

FIGS. 3D and 3E are simplified illustrations of an array of skin treatment units applied to an uneven segment of skin according to an example. Each of the skin treatment units 112-1 through 112-3 of array 108 has a freedom of translational movement as shown by arrows 346 and 348 (FIG. 3D) and arrows 352 and 354 (FIG. 3E) with respect to an adjacent unit. These translational movements are in different planes, which for simplicity of the explanations are shown as perpendicular planes. These planes are also different from plane 300 (FIG. 3A) although translational movements indicated by arrows 346 and 352 could be in plane 300, but at an angle to translational movement 304.

Figure 3F:
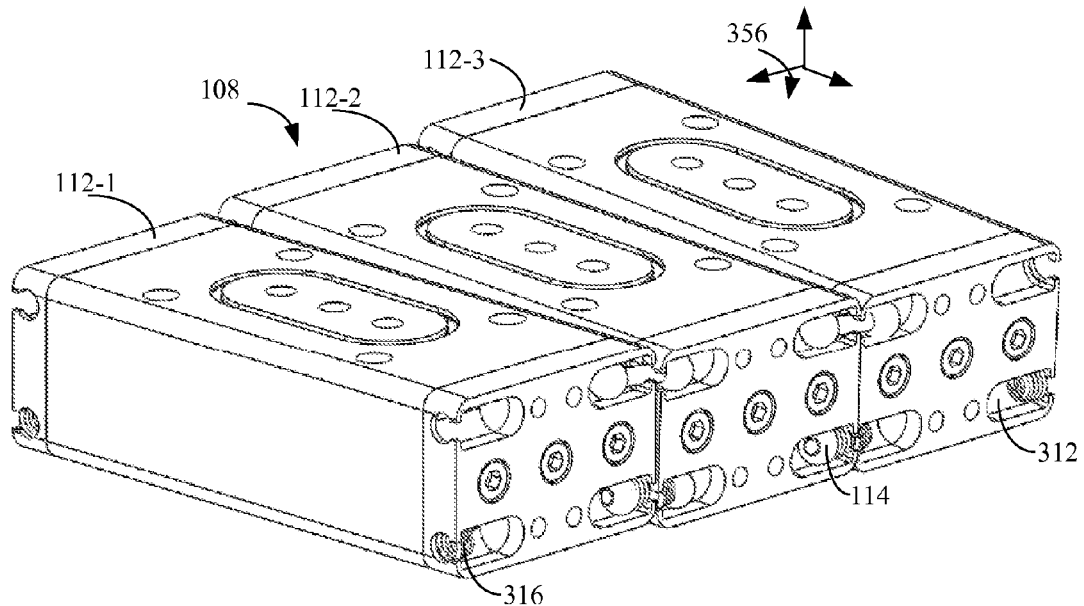
Figure 3G:
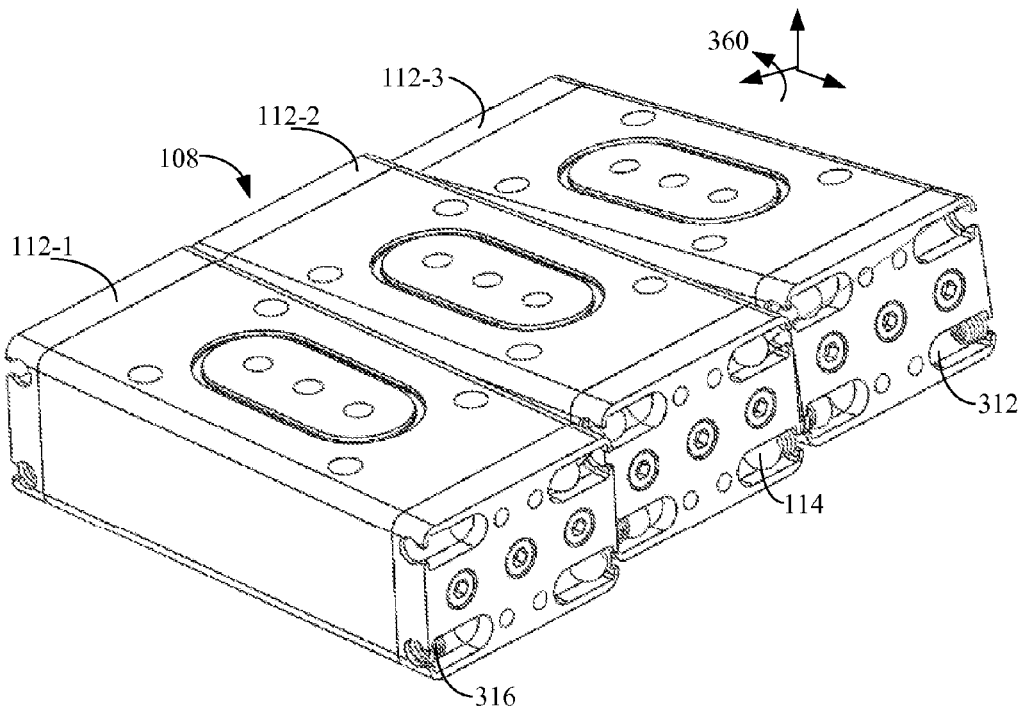

FIGS. 3F and 3G are simplified illustrations of an array of skin treatment units applied to an uneven segment of skin according to an example. Each of the skin treatment units 112-1 through 112-3 of array 108 has a freedom of rotational movement as shown by arrow 356 (FIG. 3F) and arrow 360 (FIG. 3G) with respect to an adjacent unit. These rotational movements are in a plane different from planes in which rotational movements indicated by arrows 336, 340, 342, and 344 take place (FIGS. 3B and 3C).

Joint 114 (FIG. 1 and FIG. 3) could be a dog-bone type joint that facilitates the described above movements. Joint 114 is subject to a stretch sufficient to support these translational and rotational movements between skin treatment units 112. Other types of joints such as Cardan joint, Hooke joint, resilient elements, and other similar elements facilitating at least two degrees of rotational movement, translational movement and some of the stretch between the adjacent units could also be used. In addition, rather than utilizing joints to create the flexibility of the array, the individual units can be mounted to a flexible substrate which would allow any or all of the afore mentioned movements. In addition, the array can be created as illustrated in a single dimension, or the array can also be expanded to include two or more rows of individual units by employing any of the jointed or mounted techniques described herein as well as other techniques.

To summarize, array 108 could conform to the topography of the treated skin segment since each of the skin treatment units 112 possesses at least two rotational movements. Additional translational or linear movements of each of the skin treatment units 112 could further facilitate the ability of array 108 conforming to the topography of the treated skin segment. The dog-bone type joint, or a similar joint supporting spatial movement in almost any direction in space with respect to the adjacent skin treatment unit also helps in conforming array 108 to the topography of the treated skin segment.

Figure 4:
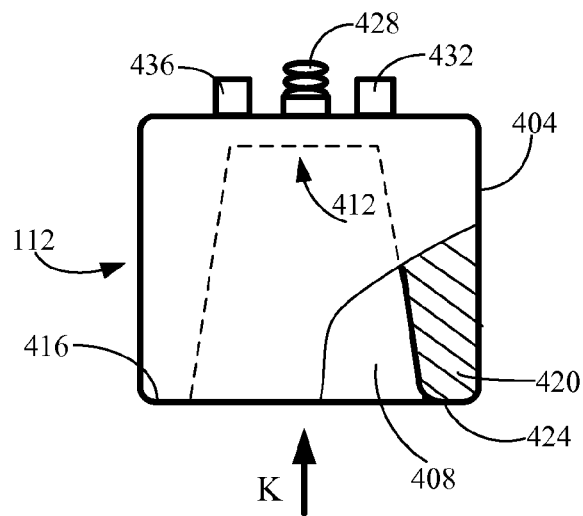
FIG. 4 is simplified side view of a skin treatment unit according to an example.

Reference is made to FIG. 4, which is a non-limiting example of a simplified side view of a skin treatment unit 112. Skin treatment unit 112 is illustrated in this example as including a housing 404, which includes a hollow interior or cavity 408 formed inside of housing 404. Cavity 408 includes an aperture or outlet located in the wall of the skin treatment unit (i.e., such as at a first end 412 or elsewhere), to connection nipple 428 to fluidly interface with a source of negative pressure such as for example, a vacuum pump 120 (FIG. 1) or a source of positive air pressure, which could be ambient atmospheric air pressure or a higher pressure produced by pump 124 (FIG. 1). A suitable valve controlled by the control unit 104 or splitter card 144 could simplify the communication. A flexible hose (not shown) may connect between first end 412 of skin treatment unit 112 and sources of negative pressure 120 and positive air pressure 124. A rim 416 terminates the second end of skin treatment unit 112. Rim 416 could have a width similar to the thickness of walls 420 of skin treatment unit housing 404; it could terminate by a gasket or other material that has a surface 424 that is substantially the same size as the rim 416 or, in other embodiments, a surface that is substantially larger than walls 420 and/or the rim 416 can be utilized. Connectors 432 and 436 schematically shown as rectangles to simply illustrate their existence, facilitate delivery of different skin treatment energies from energy sources 124 to the treated segment of skin. It should be appreciated that any of a variety of connectors can be used for this interface.

In use, surface 424 of rim 416 is applied to a treated skin segment and as such, the surface of the skin segment mated with the surface 424 operates to seal the hollow interior or cavity 408. The size of cavity 408 could be, as a non-limiting example, 20×40 or 40×80 mm in size. Surface 424 of walls 420 could be flared outwardly to increase contact area with the surface of skin to provide a better seal between surface 424 and the skin. Operating the skin treatment unit 112 includes the application and release of vacuum pressure or negative pressure to cavity 408 of the skin treatment unit 112 through the valve, connecting nipple or nozzle 428. Such operational sequence generates a back and forth massaging movement of the treated skin volume to which the surface 424 of rim 416 of the cavity is being pressed. Surface 424 of rim 416 could be coated with a low friction coating to enhance massaging of the treated skin.

In a non-limiting example, the release of the vacuum pressure to cavity 408 of the skin treatment unit 112 (which facilitates in the back and forth massaging movement of the treated skin volume against the rim of the cavity) can be assisted by venting the cavity to the surrounding ambient air. The venting could be done through the outlet connecting nipple 428. Alternatively positive air pressure may be delivered through outlet connecting nipple 428 or through another conduit or nipple (not shown). Such operation of skin treatment unit 112 would further enhance the intensity of the massaging movement. Control unit 104 (FIG. 1) could set the sequence, intensity and duration of application of the selected type of air pressure and vacuum to cavities 408.

Figure 5:
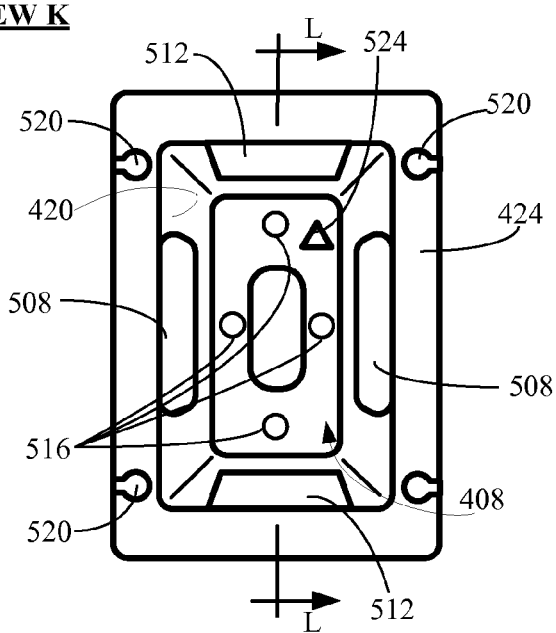
FIG. 5 is a simplified illustration of a skin treatment unit showing the unit cavity according to an example.

According to an example as illustrated best in FIG. 5, energy to skin applying elements are located on the inner surface of walls 420 of hollow interiors or cavities 408. Energy delivery elements could be such elements like RF electrodes 508, ultrasound transducers 512 (FIG. 5), light emitting objects such as Light Emitting Diodes (LEDs) 516 or laser diodes, optical fibers conducting laser light into the cavities, and other elements delivering different types of skin treatment energy to the skin. A skin temperature sensor 524, such as a thermistor, a thermocouple or a non-contact sensor such as an optical pyrometer as non-limiting examples, could be located in the hollow interior or cavity 408. The temperature sensing elements 524 can also or alternatively be located at other locations in the cavities or on the rim to get a sensing of skin temperatures at different locations. In another example, the cavity or parts of the cavity and/or the energy delivery surfaces can be made of thermally conductive materials. During the treatment procedure, these parts made of thermally conductive material come to a thermal equilibrium with the skin. Temperature sensors can be inserted into these parts made of thermally conductive materials and can give indication of average skin temperature over these areas, which is useful for treatment control. Numeral 312 (in FIG. 3) and illustrated as element 520 in FIG. 5 refer to nests or a receptacle for accepting dog-bond type joints 114 or similar joints connecting between individual skin treatment units 112 of array 108 (FIG. 1) and facilitating the at least two degrees of rotational movement and two translational movements in different planes between skin treatment units 112 such that their spatial location can conform array 108 to the topography of the treated skin segment.

Figure 6:
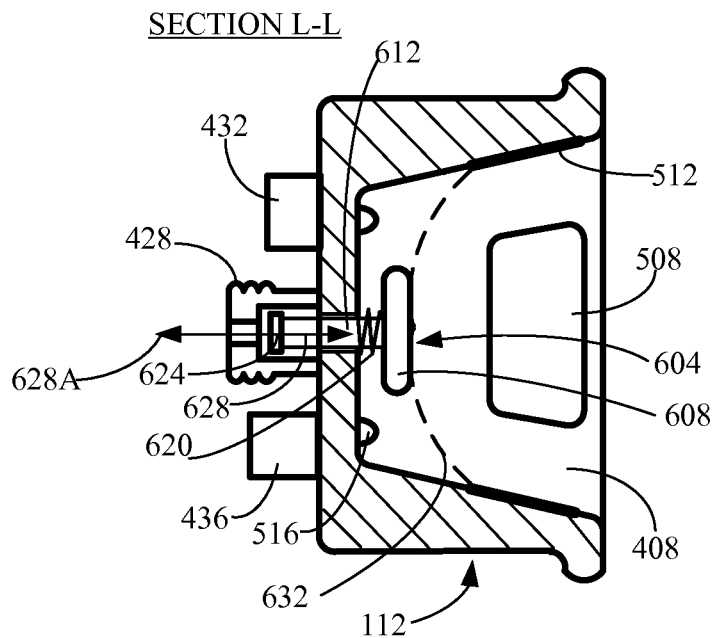
FIG. 6 is a simplified cross section of a skin treatment unit of FIG. 4 according to an example.

Reference is made to FIG. 6, which is a cross section view of a skin treatment unit of FIG. 5 at the line L-L. Valve 604, which could be such as a valve disclosed in Patent Cooperation Treaty Publication WO2010/007619 by the same inventor and assigned to the same assignee and incorporated by reference above, is an assembly of a plate 608 and plunger 612, with spring 620 and a stopper disk 624. Alternatively, the valve 604 could be a solenoid valve or other valve mechanism. Plate 608 and plunger 612 of valve 604 have a freedom of linear movement in the axial direction as indicated by arrow 628. When the source of negative pressure 120 is applied to the valve 604, a negative force or vacuum is created within the hollow interior or cavity 408 such that if the rim of the skin treatment unit is pressed against the surface of the skin, a volume of skin is drawn into the cavity 408 forming a skin protrusion shown by broken line 632. The protrusion pushes plate 604 and plunger 612 with stopper disk 624 in the direction indicated by arrow 628A until it closes outlet connection nipple 428. As the negative pressure in cavity 408 falls, the protrusion recedes restoring the fluid/air connection with vacuum pump 120 (FIG. 1) thereby again opening the valve 604 to allow the application of the negative pressure. This repeated action of valve 604 regulates the level of vacuum pressure in the cavity and thus, the magnitude of the protrusion of skin being drawn into the cavity. Other valve 604 structures such as two mated cones or two mated spheres are also anticipated.

Figure 7:
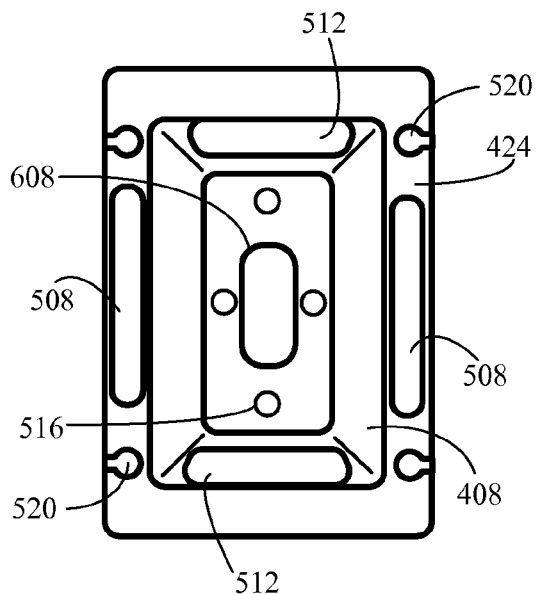
FIG. 7 is a simplified illustration of a skin treatment unit showing the unit cavity according to an example.
Figure 8:
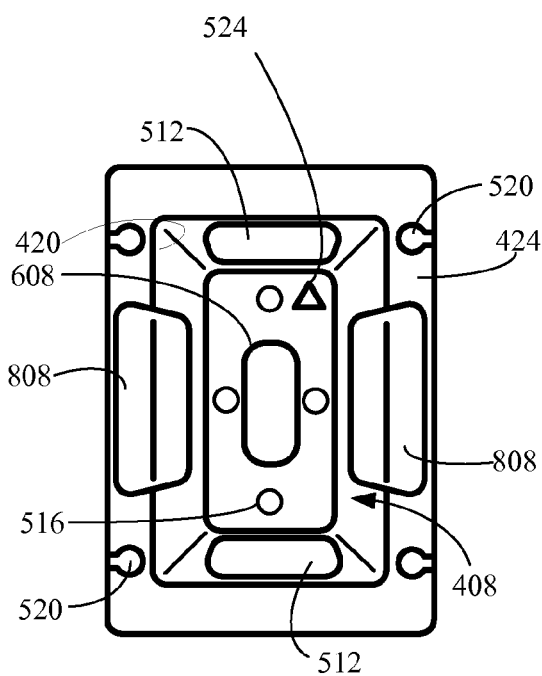
FIG. 8 is a simplified illustration of a skin treatment unit showing the unit cavity according to an example.

According to one example, RF electrodes 508 could be located on the external surfaces of the skin treatment unit such as for example, surface 424 (FIG. 7). According to one example, RF electrodes 808 (FIG. 8) can extend beyond the inner surface of the cavity walls 420, sealing edges 424 of which could be flared outwardly to provide extended RF energy delivery surfaces and apply RF energy to heat not only the tissues within cavity 408, but to adjacent skin tissue about to be drawn into the cavities as well. According to one example, RF electrodes 508 could be located almost along the entire perimeter surface 424 (FIG. 7).

Figure 9A:
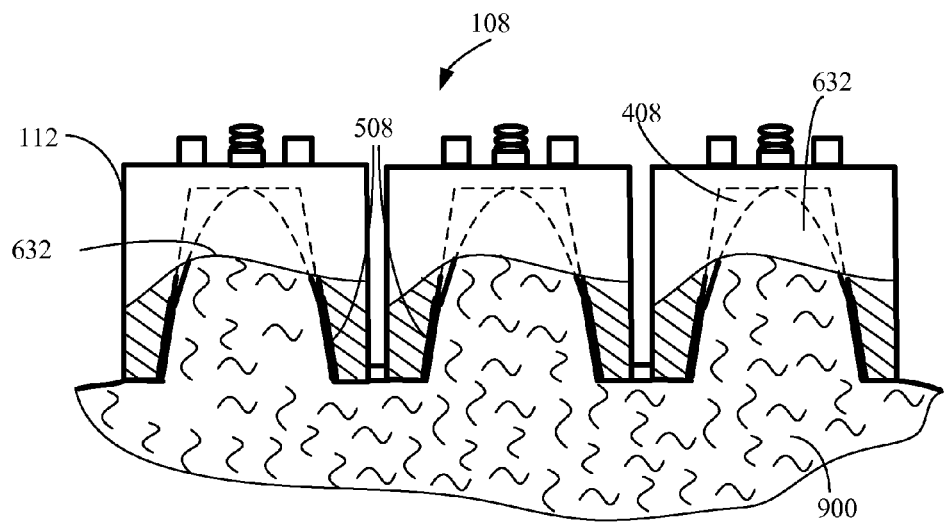
FIGS. 9A and 9B, collectively referred to as FIG. 9, are simplified illustrations of RF electrode connections and operation according to an example.
Figure 9B:
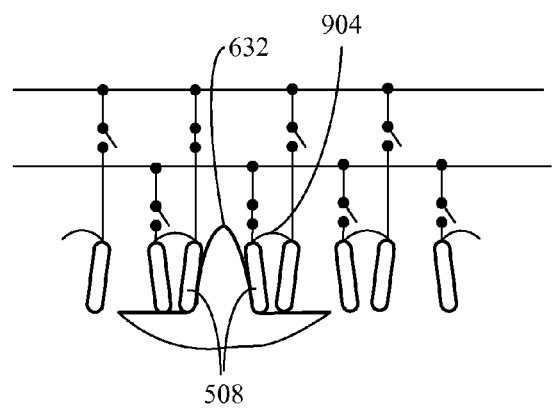

FIG. 9 is a simplified illustration of RF electrode connections and operation according to an example. Array 108 is applied and fixed to a large segment of skin 900 such that it conforms to the large segment of skin topography. Vacuum pump 120 (illustrated in FIG. 1) generates a negative pressure within the hollow interiors or cavities 408 of skin treatment units 112 of about −0.1 bar to −0.9 bars, as a non-limiting example. The negative pressure or vacuum draws individual skin volumes into cavities 408 of skin treatment units 112 of array 108 and forms skin protrusions 632 within the cavities 408. As skin protrusion 632 grows in size, it occupies a larger volume of the cavity 408, and spreads in a uniform way inside of the cavity. Control unit 104 (illustrated in FIG. 1) activates the supply of skin treatment energy to the RF electrodes only when a firm contact between the skin protrusion 632 and the RF electrodes 508 is established. The proximate electrodes 508 located on the inner surfaces of hollow interiors or cavities 408 of adjacent skin treatment units 112 are connected together (FIG. 9B) by a connection 904 and switching done independently and symmetrically for each of the cavities. Such connection of adjacent RF electrodes increases the effective surface of the electrode and facilitates homogenous heat in the treated skin segment distribution. The back and forth massaging movement of the skin (FIG. 12) further contributes to homogenous heat within the skin distribution and prevents formation of "hot spots." Control unit 104 or splitter card 144 (FIG. 1) could control the RF energy supply to RF electrodes and the RF electrodes switching process. To avoid erroneous or the inadvertent supply of RF energy to the skin, a hardware interlock of RF delivery to RF electrodes could be implemented. Protrusion signal generated by valve 604 (FIG. 6) operative in each of cavities 408 could serve to activate/de-activate the supply of RF energy and also increase the treatment process safety.

Figure 10:
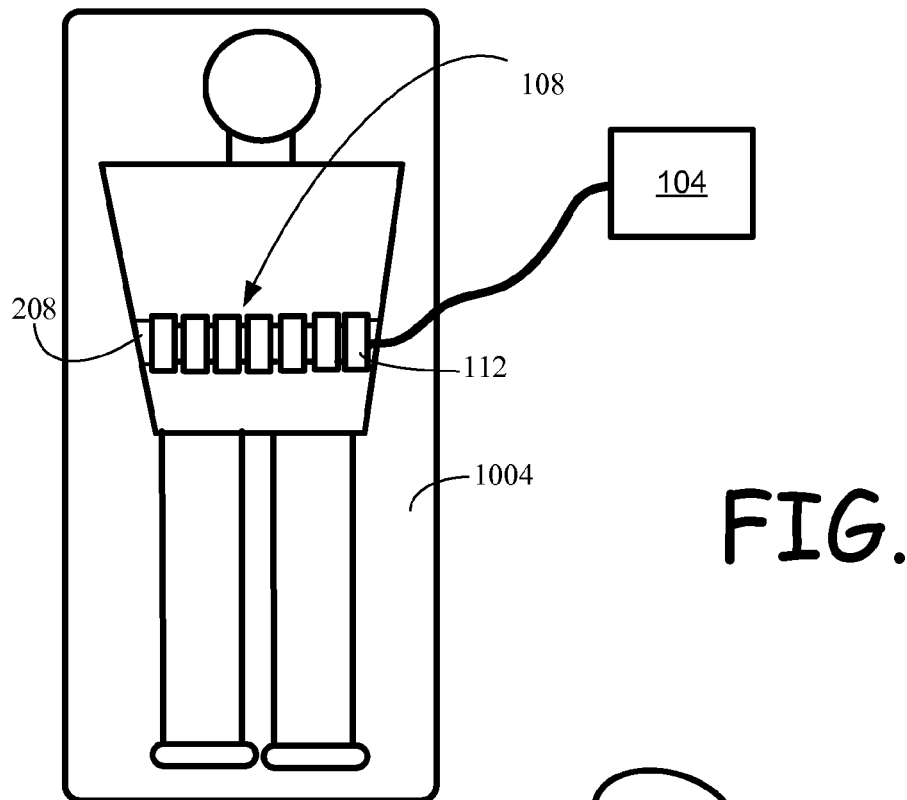
FIG. 10 is a schematic illustration of a subject that wears array 104 according to an example.

One of the applications of the present array is the massaging of large segments of skin. FIG. 10 is a schematic illustration of a subject that wears array 108 according to an example. The subject lies on a massage bench 1004. Array 108 is applied to a large segment of skin, for example, to the abdomen of a treated subject and attached to the skin with the help of mount 208. The mount is sized and shaped to couple and fix array 108 to a treated skin segment. Mount 208 could be a belt type mount. Proper cables and tubing could be employed to connect the array to control unit 104 and each of the skin treatment sources. Since belt mount 208 couples and fixes array 108 to a treated skin segment, the caregiver maintains mobility and his hands are free. The caregiver could concurrently be involved in additional activities without affecting the treatment process.

Although shown as a one dimensional array 112, apparatus 108 could include arrays which are two dimensional arrays or matrix type arrays and arranged in a variety of patterns.

Figure 11:
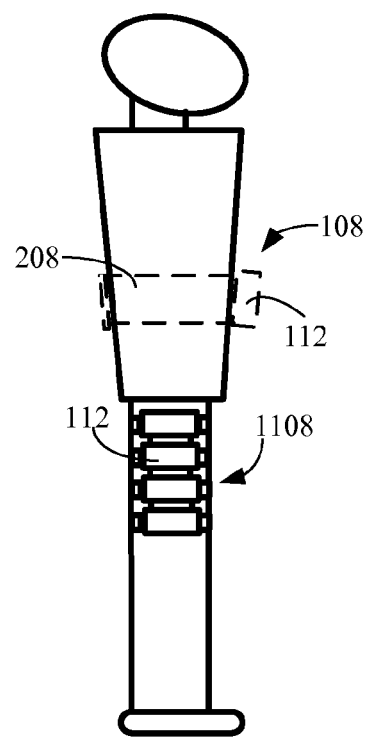
FIG. 11 is a schematic illustration of a subject that wears a similar array according to an example.

FIG. 11 is a schematic illustration of a subject that wears a similar array according to an example. Array 1108 is similar to array 108. It includes a plurality of skin treatment units 112 and is configured to be worn on a limb, in this case a leg, of the treated subject. In a similar manner the array could be configured to be applied to a large segment of skin and treat or massage the lower or upper back, chest or other segments of the treated subject body. Proper cables and tubing could be employed to connect each skin treatment unit of the array to control unit and each of the skin treatment sources. Since array 1108 is coupled and fixed to a treated skin segment, the caregiver maintains mobility and his hands are free. The caregiver could concurrently be involved in additional activities without affecting the treatment process.

As shown in FIG. 11, more than one array could be used to treat simultaneously or according to a pretreatment protocol a plurality of large skin segments of the treated subject. For instance, in FIG. 11, the array 1180 is illustrated as providing treatment to the upper portion of the subjects leg, while array 108 including skin treatment devices 112 connected mount 208 treats the torso.

Figure 12:
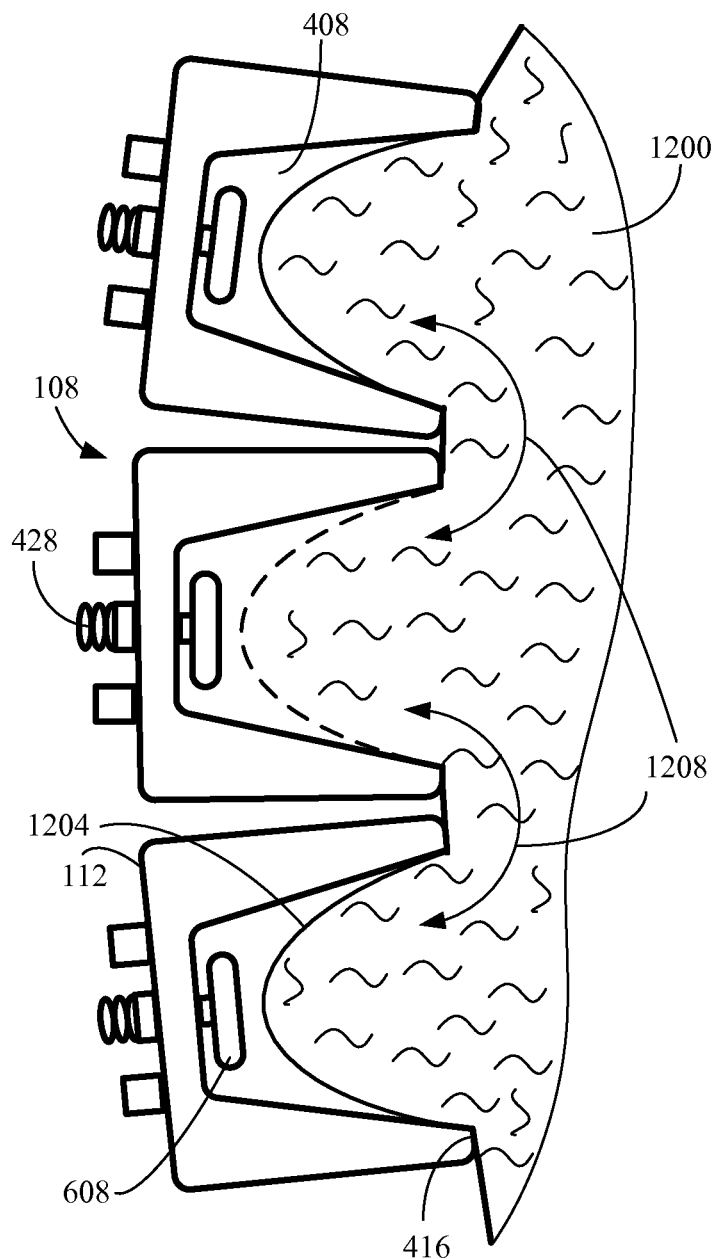
FIG. 12 is a schematic illustration of a massaging action of an array according to an example.

FIG. 12 is a schematic illustration of a massaging action of an array according to an example. Array 108 is applied and fixed to a large segment of skin 1200 such that it conforms to the topography or contour of the large segment of skin. Vacuum pump 120 (illustrated in FIG. 1) generates a negative pressure within the hollow interiors or cavities 408 of skin treatment units 112. As a non-limiting example, the negative pressure is about −0.1 bar to −0.9 bars. Each of the cavities 408 is individually controlled and connected to vacuum pump 120 and as such vacuum pressure could be supplied simultaneously to all of the cavities 408 or according to a selected treatment protocol to a number of cavities 408. The negative pressure or vacuum draws individual skin volumes into cavities 408 of array 112 and forms in appropriate cavities skin protrusions 1204. As skin protrusion 1204 grows, it occupies a larger volume of cavity 408, and spreads inside the cavity and eventually pushing the valve 428 closed by moving plunger 508. Adjacent or more remotely located skin treatment units are subject to similar sequential application and release of vacuum. This sequential application and release of vacuum to the cavities 408 of the skin treatment units 112 generates suction that draws and releases volumes of skin into the cavities generating in respective cavities skin protrusions 1204. The volumes of skin drawn and released are smaller than the treated skin segment 1200 to which array 108 is applied and fixed. The sequential application and release of the vacuum pressure generates (as shown by arrows 1208) a back and forth massaging movement of at least a portion of the large skin segment against the flared rims 416 of the skin treatment units 112. Sequential application of the vacuum pressure alone achieves or imparts the massaging movement of skin to a large segment of skin. Additional positive pressure produced by a pump 124 (as illustrated in FIG. 1) to a cavity when the vacuum phase is finished can enhance skin movement out of the cavity and therefore enhance the massage action. No other mechanical actuators and/or any moving parts are used in these illustrated embodiments. The massaging movement of skin could be applied simultaneously to a large segment of skin or according to a selected skin massaging protocol.

Skin massaging imparts on the skin a mechanical massaging energy. According to an example of the method additional types of skin treatment energy could be coupled to a large segment of skin 1204 concurrently with the application of vacuum pressure and massage. Such skin treatment energy could be energy heating the skin. As a non-limiting example, the energy may include RF energy, ultrasound energy, microwaves energy, and light energy. Different forms of energy according to different skin treatment protocols could be concurrently applied in each cavity and in different cavities.

Figure 13:
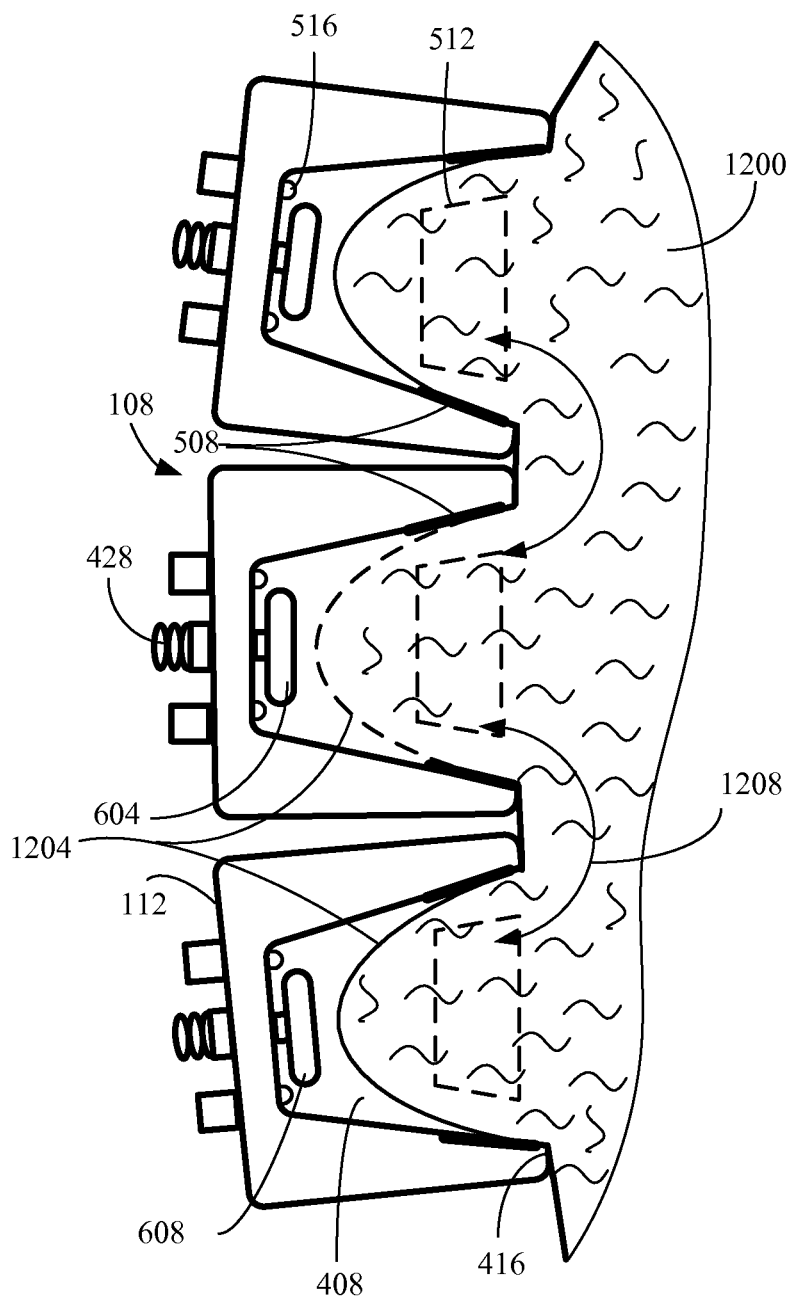
FIG. 13 is a schematic illustration of a massaging action of an array combined with application of skin treatment energy according to an example.

Reference is made to FIG. 13, which is a schematic illustration of a massaging action of an array combined with application of skin treatment energy according to an example. Safety of the application of the skin treatment energy to a subject's skin is a paramount requirement in every aesthetic and medical energy based treatment. Firm contact between energy to skin applying elements, which could be RF electrodes 508 or ultrasound transducers 512 and protrusion 1204 facilitates good energy transfer, avoids formation of hot spots on the RF electrodes, and other adverse effects. Such contact conditions exist only when skin protrusion 1204 sufficiently fills cavity 408. Sensing of protrusion magnitude (or status) could provide feedback to control unit 104 that controls one or more sources of skin treatment energy 124 supplying RF energy to electrodes 508. Valve 604 could send such "protrusion status signal" to control unit 104 (FIG. 1) when the volume of skin sufficiently fills the cavity as required for safe skin treatment energy application or coupling. Alternatively, optical, resistive, capacitive, inductive sensors or any other types of sensors that is suitable for the direct or indirect detection of the protrusion magnitude could be implemented.

When firm contact between skin protrusion 1204 and electrodes 508 is established, control unit switches ON skin treatment energy source 124 (FIG. 1), which could be an RF generator as a non-limiting example. RF generator could be a single generator supplying RF energy to the skin treatment units according to a desired skin treatment protocol or it could be a plurality of RF generators with each generator providing RF energy to a corresponding skin treatment unit. RF energy is supplied to drawn into cavity 408 skin volume or protrusion 1204. RF induced current heats the skin volume 1204 and produces or enhances the desired skin treatment effect, which could be adipose tissue reduction, body shaping, skin tightening and rejuvenation, contraction of collagen fibers and other aesthetic skin treatment effects. Firm contact between electrodes 508 and skin protrusion 1204 could be detected during the RF energy treatment by monitoring skin impedance between electrodes 508. The lower the skin impedance at the beginning of treatment, the better is the contact between the RF electrodes and the skin forming protrusion 1204.

Commonly RF frequency could be in the range from 50 KHz to 200 MHz. Typically, RF frequency is from 100 KHz to 10 MHz or from 100 KHZ to 100 MHz or, alternatively, from 300 KHz to 3 MHz. The RF power could be in the range from 0.5 W to 300 W. Typically, the range of the RF power is from 1 W to 200 W or from 10 W to 100 W and it could be coupled into the skin in a pulsed or continuous mode or some other form of modulated delivery. RF induced current heats the individual skin volumes 1204. The heating could be non-homogenous and different skin volumes could be heated to different and sometimes not desired temperatures. The control unit is operative to govern the source or sources of skin treatment energy, which in this example are one or more RF generators. The control unit sets a skin treatment protocol and synchronizes the skin treatment protocol with the massaging movement, such that it homogenizes the skin treatment energy distribution across the large segment of skin. In addition housings 404 of skin treatment units 112 are made of thermally conductive material that further enhances and homogenizes heat distribution across the large segment of skin.

In one example, skin treatment units 112 in addition to RF electrodes 508 could include energy to skin applying elements operative to apply other or additional types of skin treatment energies. Such energies could be for example, ultrasound energy applied to the protrusion or volume of skin drawn into cavity 408 by transducers 512 (FIG. 4) or Light energy applied by LEDs 516 or other devices.

Further, in one example, control unit 104 (FIG. 1) switches ON skin treatment energy source 124, which could be an ultrasound generator, only when firm contact between skin protrusion 1204 and transducers 512 is established. Ultrasound energy is supplied to the skin volume 1204 that has been drawn into cavity 408. In one example, ultrasound could be used to preheat the treated skin volume 1204 and reduce its resistance, such that induced RF current will preferentially pass through preheated skin volume 1204 segments and enhance the desired skin treatment effect, which could be adipose tissue reduction, body shaping, skin tightening and rejuvenation, contraction of collagen fibers and other aesthetic skin treatment effects. Firm contact between transducers 512 and skin protrusion 1204 could be detected during the ultrasound energy treatment by depositing on the transducers a thin conductive layer not attenuating the ultrasound energy and monitoring skin impedance between the transducers.

In one example, moderately focused ultrasound is used to impart a movement on the adipose tissue cells constituents that have a different density. The movement causes rupture of the cell walls and destroys the adipose tissue cells.

Typically, the range of ultrasound energy frequency is from 500 kHz to 5 MHz. Typically, the range of ultrasound power density is 0.1 W/cm2 up to 5 W/cm2.

The described above apparatus and method could be used for aesthetic treatments such as adipose tissue reduction, body shaping, skin tightening and rejuvenation, contraction of collagen fibers and other aesthetic skin treatment treatments.

It should be noted, however, that other and additional combinations of skin treatment energy and massage could be used to for skin treatment. These other forms of energy and massage are within the scope of the present disclosure and the claims.

What is claimed is:

1. An apparatus comprising:
    an array of connected skin treatment units, each of the individual skin treatment units in the array comprising a cavity, wherein the application of a vacuum pressure to each individual skin treatment unit is individually controlled by a controller communicating with a valve located inside a cavity of a skin treatment unit, each valve regulating the level of the vacuum in the cavity based at least in part on the volume of skin protrusion inside the cavity in the skin treatment unit and the skin treatment unit adapted to be applied to a skin segment together with each of the other skin treatment units and comprising:
        a housing defining the cavity that fluidly communicates with a common source of negative pressure, with one side of an interior of the housing terminated by a rim adapted to facilitate a sealing of the cavity when the skin treatment unit is applied to the skin, the dimensions of the defined cavity adapted to be sufficient to accommodate a volume of a skin segment drawn into the defined cavity by the source of negative pressure to create a skin protrusion and wherein the skin treatment units are adapted such that repeated application and release of the negative pressure to adjacent skin treatment units generates a back and forth massaging movement of the treated skin volume against the rim of the cavity and against rims of adjacent skin treatment units resulting in a massaging movement of at least a portion of the volume of skin against at least one rim;
    in each cavity, an energy to skin applying element to apply a skin treatment energy to the respective skin protrusion; and
    associated with each cavity, a temperature sensor configured to detect a temperature of the respective skin protrusion;
    wherein the controller is further configured to individually apply the skin treatment energy to the skin protrusion based on the temperature of the respective skin protrusion;
    wherein the connection between at least two individual skin treatment units is jointed so that each of the skin treatment units of the array of individual treatment units has at least two degrees of rotational movement with respect to an adjacent skin treatment unit so that the array is adapted to conform to the various topographies of the skin segments.

2. The apparatus according to claim 1, wherein the joint between at least two adjacent skin treatment units of the array is configured to allow at least two translational movements with respect to the adjacent skin treatment unit and wherein said translational movements are in different planes.

3. The apparatus according to claim 1, wherein the joint between at least two adjacent skin treatment units of the array is configured to support spatial movement of the skin treatment units in almost any direction in space with respect to each other.

4. The apparatus according to claim 3, wherein the joint between at least two adjacent skin treatment units of the array can be stretched thereby allowing movement of the adjacent skin treatment units with respect to each other.

5. The apparatus according to claim 3, wherein the joints between at least two adjacent skin treatment units render the array operative to treat at least one of a group of skin segments consisting of abdomen, limbs, shoulder, lower back, and upper back.

6. The apparatus according to claim 1, wherein the joints between at least two adjacent skin treatment units of the array renders the array a variable length array.

7. The apparatus according to claim 6, wherein the variable length array further comprises a variable length mount adapted to be sized and shaped to couple and fix the array to a treated skin segment such that the array can be worn.

8. The apparatus according to claim 1, wherein the rim of the defined cavity is coated with a low friction coating to enhance the massaging movement of the treated skin segment.

9. The apparatus according to claim 1, wherein each of the skin treatment units includes a valve located inside the cavity, the valve regulating the pressure level of the vacuum in the defined cavity and thus affecting the magnitude of the protrusion drawn into the defined cavity.

10. The apparatus according to claim 1, wherein the skin volume drawn into the defined cavity of the skin treatment unit is released by at least one action selected from a group actions comprising releasing of the negative pressure, reduction of the negative pressure, venting the defined cavity and applying a positive air pressure to the defined cavity.

11. The apparatus according to claim 1, further comprising a processing unit configured to govern the operation of at least the source of negative pressure and at least one skin treatment energy source in accordance with a skin treatment protocol.

12. The apparatus according to claim 11, wherein the skin treatment protocol is at least one of a group of protocols consisting of a continuous delivery of the skin treatment energy and pulse delivery of the skin treatment energy.

13. The apparatus according to claim 11, wherein the controller is further configured to control each of the skin treatment units and synchronizes the delivery of the skin treatment energy and the application of vacuum pressure to homogenize the skin treatment energy distribution across a large segment of skin.

14. The apparatus according to claim 13, wherein the housing of the skin treatment unit is constructed of a thermally conductive material to further facilitate the skin treatment energy distribution and homogenization across the large segment of skin.

15. The apparatus according to claim 1, wherein the energy to skin applying elements apply to the protrusion at least one of a group of skin treatment energies consisting of RF energy, ultrasound energy, microwave energy, and light energy.

16. The apparatus according to claim 15, wherein the energy to skin applying elements are at least one of a group of elements consisting of RF electrodes, ultrasound transducers, LEDs, incandescent lamps, Xenon lamps and lasers.

17. The apparatus according to claim 15, wherein RF electrodes of adjacent skin treatment units are located on the inner surfaces of hollow cavities of adjacent skin treatment units are connected together by a connection and switched independently and symmetrically for each of the cavities to increase an effective electrode surface.

18. The apparatus according to claim 1 and wherein the skin temperature sensor is one of a group of sensors consisting of a thermistor, a thermocouple, or and a noncontact optical sensor.

19. The apparatus according to claim 18, wherein the skin temperature sensor is located in one of a group of locations consisting of a defined cavity and on a rim of the defined cavity.

20. The apparatus according to claim 1, wherein massaging movement of the large segment of skin simplifies and reduces caregiver effort by reducing an amount of movements of the array by the caregiver.

21. The apparatus according to claim 1, wherein the controller is at least one of a processor unit, a splitter card or a controllers each attached to an individual skin treatment unit.

22. A device configured to provide automated massaging of a skin segment, the device comprising:
  a housing that defines a cavity, an interface to the skin segment and a pressure source interface, the interface to the skin segment includes a rim adapted to be applied to the skin segment and, which when pressed against the skin segment is configured to substantially seal the defined cavity such that negative pressure individually controlled through the pressure source interface allows pressure to be applied to draw a portion of the skin segment into the defined cavity and forms a protrusion, and release of the negative pressure allows the portion of the skin segment to at least partially vacate the defined cavity;
  an interface to a source of skin treatment energy;
  one or more surface on the housing adapted to come in contact with the skin protrusion and connectivity between the interface to the source of skin treatment energy and the one or more surface such that skin treatment energy can be applied to the skin segment through the one or more surfaces;
  a temperature sensor configured to detect a temperature of the skin protrusion; and
  a controller configured to control the application of the skin treatment energy based on the temperature of the skin protrusion;
  wherein the pressure source interface includes a valve located inside the cavity, the valve regulating the level of the vacuum in the defined cavity based on the volume of the protrusion, such that as the volume of the protrusion increases, the negative pressure is released and as the volume of the protrusion decreases, the negative pressure is applied and,
  wherein the device includes a dog-bone type joint for connecting the device to additional devices but, that allows movement of the connected devices relative to each other to facilitate conformation of the connected devices to the topography of the skin segment.

* * * * *